United States Patent
Love et al.

(10) Patent No.: US 8,359,084 B2
(45) Date of Patent: Jan. 22, 2013

(54) CONTAINMENT TUBES AND IMAGING SYSTEMS EMPLOYING SAME

(75) Inventors: Alan Love, Chesterland, OH (US); King C. Li, Houston, TX (US)

(73) Assignee: Koninklijke PHilips Electronics N.V., Eindhoven (NL)

( * ) Notice: Subject to any disclaimer, the term of this patent is extended or adjusted under 35 U.S.C. 154(b) by 1306 days.

(21) Appl. No.: 12/056,950

(22) Filed: Mar. 27, 2008

(65) Prior Publication Data
US 2008/0300479 A1 Dec. 4, 2008

Related U.S. Application Data

(63) Continuation of application No. PCT/IB2006/053523, filed on Sep. 27, 2006.

(60) Provisional application No. 60/803,754, filed on Jun. 2, 2006.

(51) Int. Cl.
*A61B 5/055* (2006.01)

(52) U.S. Cl. ........ 600/415; 600/310; 600/410; 324/318; 5/601; 5/620; 5/627

(58) Field of Classification Search .................. 600/407, 600/410, 415, 310; 324/318
See application file for complete search history.

(56) References Cited

U.S. PATENT DOCUMENTS

| | | | | |
|---|---|---|---|---|
| 6,283,123 | B1 * | 9/2001 | Van Meter et al. | 128/205.26 |
| 6,798,201 | B2 | 9/2004 | Kuth | |
| 6,944,485 | B1 * | 9/2005 | Van Meter et al. | 600/310 |
| 6,946,842 | B2 * | 9/2005 | Gozansky | 324/318 |
| 7,167,001 | B2 * | 1/2007 | Gewiese | 324/318 |
| 2003/0125649 | A1 * | 7/2003 | McIntosh et al. | 601/15 |
| 2006/0247487 | A1 * | 11/2006 | Arts et al. | 600/21 |
| 2009/0216299 | A1 * | 8/2009 | Dantus | 607/89 |

FOREIGN PATENT DOCUMENTS

| | | |
|---|---|---|
| DE | 1566654 | 8/1970 |
| DE | 19639975 C1 | 5/1998 |
| DE | 10049414 A1 | 5/2002 |
| DE | 102004007427 A1 | 9/2005 |
| DE | 102004008343 A1 | 9/2005 |

* cited by examiner

*Primary Examiner* — Tse Chen
*Assistant Examiner* — Baisakhi Roy

(57) ABSTRACT

An isolation system with imaging or radiation therapy capability is disclosed. At least one containment barrier (14, 15, 16, 17) defines an isolation region (10). An imaging or therapy system (20) is disposed outside of the isolation region. The containment barrier includes a substantially hollow tubular extension (24, 42, 44, 124, 224, 324) protruding away from the isolation region (10). The substantially hollow tubular extension surrounds an interior volume (26) that is in fluid communication with the isolation region and is in fluid isolation from the imaging or therapy system. The substantially hollow tubular extension is made at least partially of a material providing operative communication between the imaging or therapy system and the interior volume of the substantially hollow tubular extension.

10 Claims, 14 Drawing Sheets

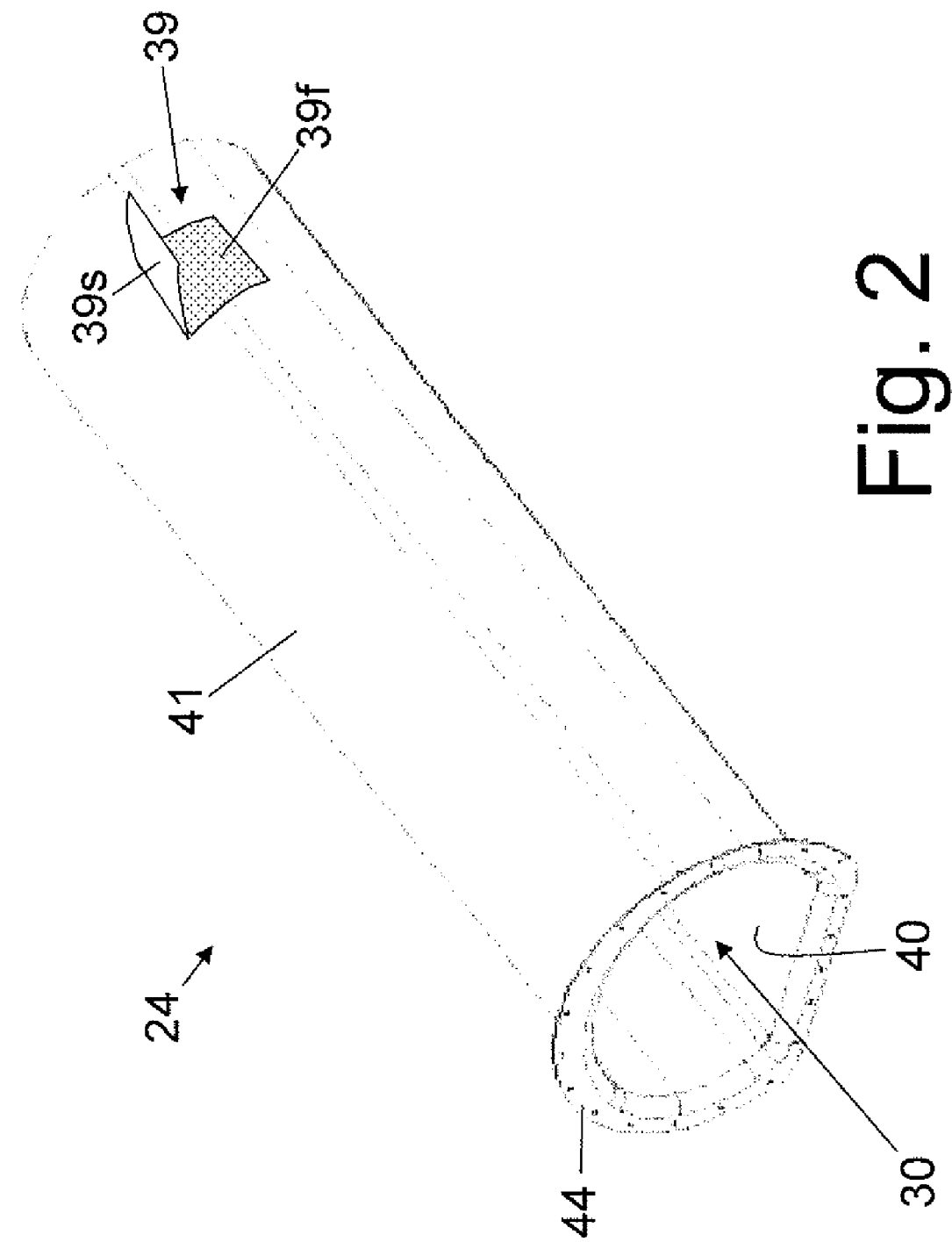

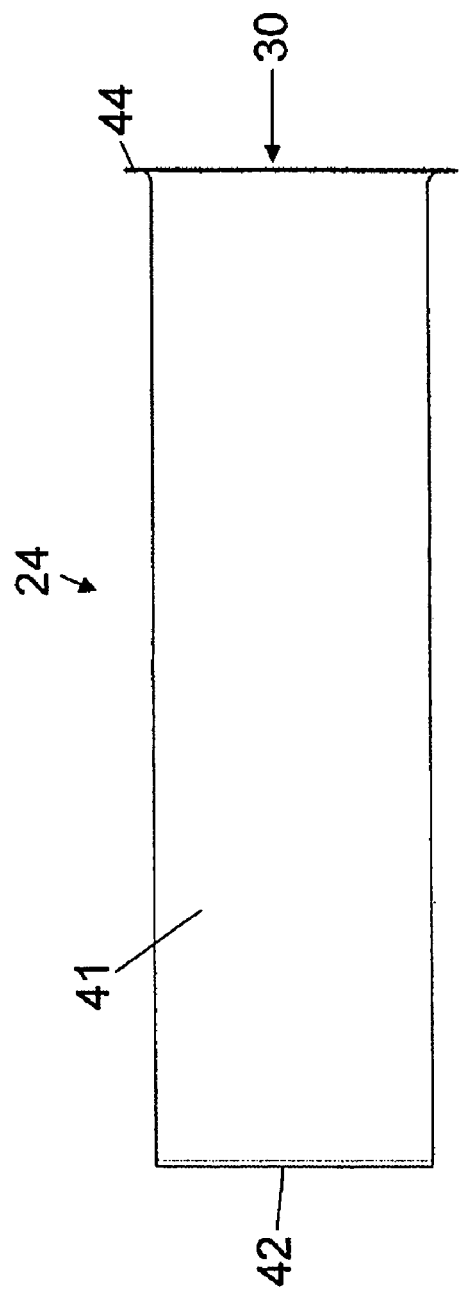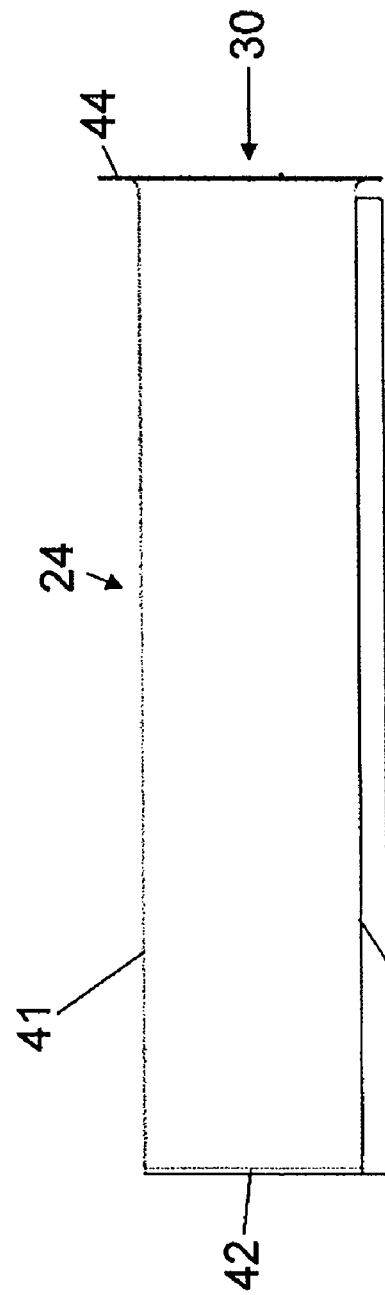

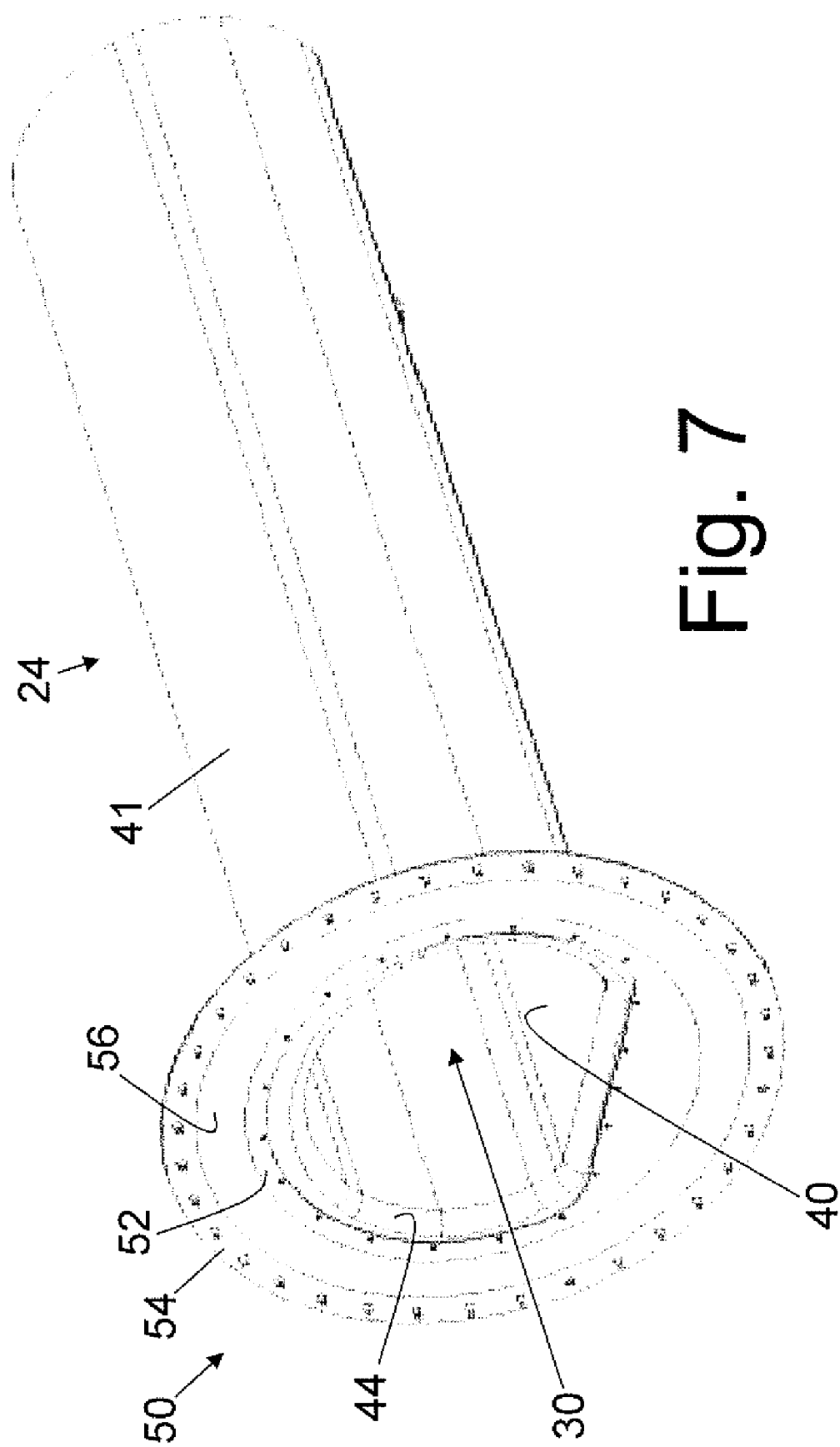

CONTAINMENT TUBES AND IMAGING SYSTEMS EMPLOYING SAME

CROSS REFERENCE TO RELATED APPLICATIONS

This application is a continuation of International Application No. PCT/IB2006/053523 filed Sep. 27, 2006 which claims the benefit of U.S. Provisional Application No. 60/803,754 filed Jun. 2, 2006.

This invention was made with Government support under grant no. N01-A0-60001 awarded by the National Institutes of Health (NIH). The Government has certain rights in this invention.

BACKGROUND OF THE APPLICATION

The following relates to the environmental arts, and to the imaging, diagnostic, characterization, and related arts. It finds particular application in diagnostic imaging of medical test subjects in biological isolation environments, and is described with particular reference thereto. However, the following finds more general application in imaging of subjects of substantially any type in substantially any isolation environment, and finds still more general application in enabling access to subjects in substantially any isolation environment for substantially any imaging, diagnostic, characterization, or other purpose without breaking the isolation and without exposing the imaging, diagnostic, characterization, or other equipment to the isolation environment.

Concerns about bioterrorism, spread of contagions by travel, and so forth have motivated development and expansion of biological isolation laboratories for research, diagnosis and monitoring of contagion outbreaks, and so forth. Dangerous infectious diseases are advantageously studied in laboratories operating at Biological Safety Level 4 (BSL-4) or in accordance with other biological safety protocols such as those specified in the BioSafety in Molecular and Biomedical Laboratories (BMBL) standard issued by the Office of Health and Safety of the Centers for Disease Control (BMBL $4^{th}$ edition available at http://www.cdc.gov/od/ohs/biosfty/bmb14/bmb14toc.htm). As noted in the introduction of the BMBL, "Microbiological laboratories are special, often unique work environments that may pose identifiable infectious disease risks to persons in or near them. Infections have been contracted in the laboratory throughout the history of microbiology." These laboratories are specially designed and constructed for containment. A typical BSL-4 laboratory is made gas-tight and coated with a thick epoxy seal on walls, floors, and ceilings, and is typically housed in a double-walled concrete structure with limited access. Mechanical systems are specially designed with redundancies and to maintain a bioseal. BSL-4 containment is achieved at least in part using a dynamic system of pressure differentials, maintained by surrounding the laboratory horizontally and vertically with a series of increasing pressure zones. Airlocks are used at primary access points. Materials used in a BSL-4 laboratory are selected to withstand exposure to decontamination chemicals such as Microchem and TB Quat, and are further selected to withstand exposure to decontamination gases such as para-formaldehyde, vaporized hydrogen peroxide at relatively high (e.g. 35%) concentration, ammonium carbonate, and so forth.

Medical imaging systems such as magnetic resonance (MR) scanners, gamma cameras, positron emission tomography (PET) scanner, and so forth are advantageously used to examine test subjects in the course of studying infectious diseases. For example, medical imaging can reveal tumors or other malignancies, can monitor tumor growth rates, and so forth. However, medical imaging systems are expensive, complex systems that are not readily compatible with the BSL-4 environment. For example, a typical medical imaging instrument includes components that are likely to be damaged by chemicals or gases used in decontamination. Medical imaging instruments also typically include materials and structures that have a high likelihood of trapping and retaining infectious agents such as bacteria, viruses, prions, or so forth. Servicing of medical imaging equipment disposed in a BSL-4 environment is also problematic—servicing technicians qualified to perform the maintenance may not be qualified to operate in the BSL-4 environment, and transferring parts into and out of the BSL-4 environment is difficult. Additionally, the isolation suits worn by personnel in the BSL-4 environment reduce manual dexterity and inhibit mobility which further increases the difficulty in maintaining medical imaging equipment in a BSL-4 environment.

SUMMARY OF THE INVENTION

In accordance with one aspect, an apparatus is disclosed, including an imaging or therapy system and a container that is sealed off from the imaging or therapy system and open to an isolation region to admit a subject from the isolation region into the container for imaging or therapy by the imaging or therapy system.

In accordance with one aspect, a subject loading system is disclosed for loading a subject disposed in an isolation region into an imaging or therapy system disposed outside the isolation region. The subject loading system includes a container sized to receive the subject. The container is sealed except for an opening arranged to provide access to an interior of the container from the isolation region. The opening is sized to admit the subject into the interior of the container. The interior of the container is in operative communication with the imaging or therapy system.

In accordance with another aspect, an isolation system with imaging or radiation therapy capability is disclosed. At least one containment barrier defines an isolation region. The imaging or therapy system is disposed outside of the isolation region. The containment barrier includes a substantially hollow tubular extension protruding away from the isolation region and overlapping an examination or processing region of the imaging or therapy system In accordance with another aspect, a method is disclosed of manufacturing a tubular member. A plurality of plates are formed having a selected cross-section. The plates are secured together to define a tubular mandrel having the selected cross-section. A filament is wound around the tubular mandrel to define the tubular member. The tubular member is removed from the tubular mandrel.

In accordance with another aspect, a subject loading system is disclosed for loading a subject disposed in an isolation region into an imaging or therapy system disposed outside the isolation region. The subject loading system includes: a tubular member sized to receive the subject, the tubular member formed by the method of the preceding paragraph; a flange disposed at an access end of the tubular member, the flange being sealed to a containment barrier of the isolation region such that the interior volume of the tubular member is accessible from the isolation region; and an endcap member sealing a second end of the tubular member opposite the access end of the tubular member.

In accordance with another aspect, a mandrel is disclosed for use in manufacturing a tubular member. The mandrel includes a plurality of plates having a selected non circular cross-section. The plates are secured together to define a tubular mandrel having the selected cross-section.

In accordance with another aspect, a subject loading system is disclosed for loading a subject from an isolation region into an imaging or therapy system. The subject loading system includes: a subject loading end; a subject imaging or treatment end; and a containment tube connecting said subject loading end and said subject imaging or treatment end.

In accordance with another aspect, an apparatus is disclosed for imaging or treating an isolated subject. The apparatus includes a tubular structure that contains the subject and separates the subject from an imaging or treatment system used in the imaging or treating.

In accordance with another aspect, an isolation system is disclosed. An isolation region includes a containment barrier. An imaging or radiation therapy system is disposed outside of the isolation region and is configured to perform imaging or radiation therapy of a subject in the isolation region across the containment barrier.

In accordance with another aspect, a subject isolation system is disclosed. A container is sized to receive a human subject. A sealing portion is configured to seal the container with a human subject inside. The container sealed by the sealing portion has an exterior susceptible to decontamination, and is configured for mounting in an imaging or radiation therapy system.

One advantage resides in enabling imaging or radiation therapy of a subject disposed in an isolation region without breaking containment of said isolation region.

Another advantage resides in providing a mechanism for loading and unloading subjects from an isolation region into an imaging or radiation therapy system disposed outside the isolation region, the mechanism being readily decontaminated in accordance with BSL-4 or other protocols followed in the isolation region.

Another advantage resides in facilitating imaging or radiation therapy treatment of a subject disposed in a BSL-4 or other type of isolation region.

Another advantage resides in providing an imaging or radiation therapy system for imaging or treating subjects disposed in an isolation region, in which the imaging or radiation therapy system is disposed outside the isolation region to facilitate maintenance and to avoid placing the imaging or radiation therapy system under the decontamination or sterilization regimen employed in the isolation region.

Another advantage resides in providing a method for manufacturing a tubular member of non-circular cross-section.

Another advantage resides in providing a tubular mandrel of non-circular cross-section for manufacturing a tubular member.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIGS. 2, 3, and 4 show perspective, top, and side views, respectively, of the tubular container of FIG. 1.

FIG. 7 shows a perspective view of the tubular container of FIGS. 2-4 with the gasket of FIGS. 5 and 6 attached.

DETAILED DESCRIPTION OF THE INVENTION

Figure 1:
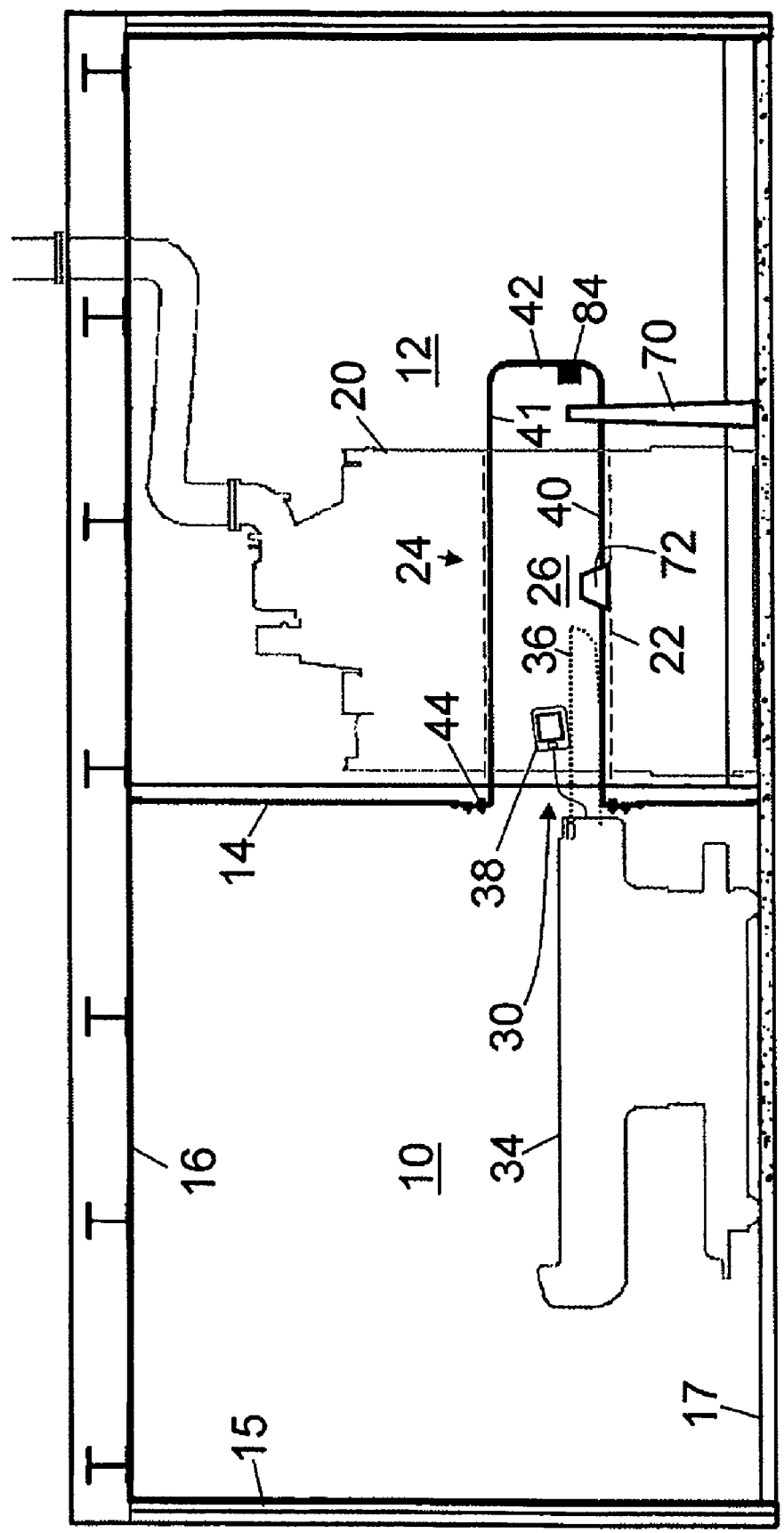
FIG. 1 diagrammatically shows an isolation region and an imaging system, along with a tubular container extension protruding from a containment barrier into an examination region of the imaging system.

With reference to FIG. 1, an imaging suite, laboratory, or the like is divided into an isolation region 10 and a less isolated or non-isolated region 12. For example, the isolation region 10 may be a "hot" side of a partitioned biological laboratory that is contaminated, or potentially may be contaminated, with a pathogen and hence is maintained in isolation in accordance with the BSL-4 protocol or another biological safety protocol. In such embodiments, the less isolated or non-isolated region 12 may be maintained at a lower isolation level, or may not be subject to any isolation protocols at all. In other embodiments, the isolation region 10 may be contaminated, or susceptible to contamination, by a toxic chemical or radioactive substance, or may be a sterile room or other isolated region that is not contaminated with anything, or so forth. The isolation region 10 is separated from the less isolated or non-isolated region 12 by a containment barrier 14 of the isolation region 12, such as the illustrated containment wall 14, or a containment ceiling, or a containment floor, or so forth. Typically, the isolation region 10 is separated by a plurality of containment barriers such as the wall 14, additional walls 15 (one of which is shown in the diagrammatic side-view of FIG. 1), a ceiling 16, and a floor 17. An airlock or airlocked door (not shown) is provided to enable ingress into and egress out of the isolation region 10 without breaking containment of the isolation region 10. Although the isolation region 10 represents a primary controlled environment, the BSL-4 controlled environment may also be considered as extending into the area outside of the isolation region 10 that is governed by isolation-related protocols such as decontamination procedures or the like.

In an example BSL-4 isolation region 10, the containment barriers 14, 15, 16, 17 are made gas-tight and coated with a thick epoxy seal on walls, floors, and ceilings, and the BSL-4 level isolation region is typically housed in a double-walled/reinforced concrete structure (not shown in FIG. 1) with limited access. Materials used in the BSL-4 laboratory are selected to withstand exposure to decontamination chemicals such as Microchem and TB Quat, and are further selected to withstand exposure to decontamination gases such as paraformaldehyde, vaporized hydrogen peroxide at relatively high (e.g. 35%) concentration, ammonium carbonate, and so forth. Although described with example reference to an isolation region that is a biological laboratory operating as a BSL-4 environment, the techniques disclosed herein for enabling imaging or radiation therapy of subjects disposed in an isolation region are applicable to substantially any type of isolation region, such as biological laboratories operating at biological safety levels other than BSL-4 such as laboratories operating at other BSL levels and under other biological safety protocols, isolation environments for processing radioactive or toxic materials, sterile isolation environments for processing patients with deficient immune systems, samples intended to remain sterile, and so forth.

An imaging or radiation therapy system 20, such as a magnetic resonance (MR) scanner, a transmission computed tomography (CT) system, a single photon emission computed tomography (SPECT) system such as a gamma camera, a positron emission tomography (PET) system, an x-ray system, an ultrasound system, an optical camera, a radiation therapy system, or a combination system such as a SPECT/PET system, a SPECT/CT system, a radiation therapy/CT system, PET/MR, or so forth, is arranged outside the isolation region 10, for example in the less isolated or non-isolated region 12. The imaging or radiation therapy system 20 has an associated examination or processing region, such as for example an examination region contained within a bore 22 (a perimeter of which example bore 22 is indicated by horizontal dashed lines in FIG. 1) of an MR scanner. A subject is disposed in the examination or processing region for imaging or radiation therapy treatment.

An arrangement such as that illustrated in FIG. 1 has diverse uses, such as for example testing of a drug for potentially treating a contagion such as an infectious bacteria, prions, or so forth. In a typical drug testing application, a matrix of test animals having a contagion that is potentially treatable with a drug under study are disposed in the BSL-4 laboratory or other isolation region 10. The isolation region 10 provides a controlled environment for testing of the contagion, and ensures that the contagion does not escape containment to infect surrounding personnel. Some animals of the matrix receive the drug under study, while others receive a lesser or greater dosage of the drug, or no drug at all. For such a drug study, the system 20 is suitably an imaging system that performs imaging or other characterization of tumors, lesions, malformations, or other physiological manifestations of the contagion. Over the course of the study, different animals of the matrix that have received different treatments (e.g., different dosages or treatment schedules of the drug under study) are periodically imaged using the imaging system 20 to determine the effect of such different treatments, as evidenced for example by growing or shrinking of the number or size of tumors, lesions, or the like.

The described drug testing application is an example. Another contemplated application is imaging or radiation therapy treatment of a patient having a deficient immune system, who is therefore kept in the isolation region 10 which is in such an application a sterile room. Another contemplated application is imaging or radiation therapy treatment of a patient who has contracted a dangerous infectious contagion, who is therefore kept in the isolation region 10 which is in such an application may for example be a BSL-4 isolation room. Other contemplated applications relate to the study or monitoring of toxic chemicals or radioactive substances, study or monitoring of unknown substances or biological entities, or so forth.

To avoid compromising the isolation (e.g., sterility, biological isolation, chemical isolation, or so forth) of the isolation region 10, the subject is loaded into the examination or processing region of the imaging or radiation therapy system 20 through a container sized to receive the subject. In the illustrated example embodiment, the container is a substantially hollow tubular extension 24 of the containment barrier 14 protruding away from the isolation region 10. The substantially hollow tubular extension 24 surrounds an interior volume 26 that includes the examination or processing region of the imaging or radiation therapy system 20. The interior volume 26 is in fluid communication with the isolation region 10 and is in fluid isolation from the imaging or therapy system 20. That is, the interior volume 26 has an airtight seal respective to the imaging or therapy system 20, but is accessible from the isolation region 10 by an opening 30.

The substantially hollow tubular extension 24 is made of a material providing operative communication between the imaging or therapy system 20 and the interior volume 26 of the substantially hollow tubular extension. For example, if the imaging or therapy system 20 includes an MR scanner portion, then at least a portion of the tubular structure 24 disposed in the examination region of the MR scanner portion is suitably non-magnetic so that the interior 26 of the tubular container 24 is in operative communication with the magnetic resonance scanner portion of the imaging system. Similarly, if the imaging or therapy system 20 includes an imaging system portion detecting ionizing radiation (for example, a SPECT or PET system), then at least a portion of the tubular container 24 disposed in an examination region of the imaging system portion detecting ionizing radiation is suitably substantially transmissive for the detected ionizing radiation so that the interior 26 of the tubular container 24 is in operative communication with the imaging system portion detecting ionizing radiation. Similarly, if the imaging or therapy system 20 includes a radiation therapy system portion emitting ionizing radiation, then at least a portion of the tubular container 24 disposed in a processing region of the radiation therapy system portion is suitably substantially transmissive for the emitted ionizing radiation so that the interior 26 of the tubular container 24 is in operative communication with the radiation therapy system portion. As yet another example, if the imaging or therapy system 20 includes an optical camera portion, then at least a portion of the tubular container 24 disposed in a viewing region of the optical camera portion is suitably substantially visually transparent so that the interior 26 of the tubular container 24 is in operative communication with the optical camera portion.

The tubular container 24 acts as a barrier between the subject and the imaging or radiation therapy system 20. For example, if the subject is diseased, then only the interior volume 26 of the tubular container 24 is exposed to the disease, and hence decontamination is suitably applied only to the interior 26 and interior surfaces 26 of the tubular container 24. The tubular container 24 should be durable and capable of containing infectious diseases or other actual or potential contamination (such as chemical contamination in the case of a toxic isolation region, or radioactive contamination in the case of a radioactive isolation region). In the case of a sterile isolation region, the tubular container 24 should be capable of preventing contaminants from entering the sterile contamination region. In the case of a biological, chemical, or radioactive isolation region 10, the tubular container 24 should also be constructed to withstand decontamination in accordance with the protocols such as BSL-4 or BMBL followed in the isolation region 10. To ensure effective decontamination, the tubular container 24 should be generally free from pockets, creases, or other areas in which contamination materials can build or pool up. The tubular structure should be mechanically able to withstand some level of impact without breaching the containment. For example, in the case of an MR scanner, if a ferrous object is brought within a certain area of the magnet, the object will be pulled toward the bore, resulting in an impact with the tubular structure.

The illustrated container 24 is generally tubular; however, other shapes can be used. A tubular shape that is cylindrical or slightly longitudinally tapered with a circular, elliptical, "D" shaped, or other cross-section advantageously reduces distance between detectors, emitters, or other operative couplings of the imaging or radiation therapy system 20 when the imaging or radiation therapy system 20 employs a generally tubular bore defining the associated examination or processing region. The at least approximate radial symmetry of a tubular container having a circular, elliptical, or "D" shaped cross-section comports effectively with detectors or radiation emitters arranged radially around the subject or arranged to rotate around the subject, and also comports effectively with the generally radial symmetry of a circular or elliptical radio frequency quadrature body coil of an MR scanner. In some embodiments, it is contemplated for the generally tubular container 24 to be sized for a particular subject, and to be changed out for subjects of different sizes. In some contemplated embodiments, the generally tubular container 24 may have some flexibility, for example allowing the tubular container 24 to be flexed with the assistance of mechanical braces disposed outside of the examination or processing region to accommodate smaller subjects. For example, such mechanical braces can compress the tubular container 24 to reduce the tubular diameter. In yet other contemplated embodiments, tubular container diameter is achieved by including a semi-rigid section with an expansion groove having a flexible joint that is held in tension by tension springs or other devices, and allows the semi-rigid section to expand when tension is removed. If flexible material is used to allow tubular container diameter adjustment, it should be selected to tolerate repetitive decontamination.

With continuing reference to FIG. 1, a subject table 34 or other subject-loading mechanism is optionally disposed within the isolation region 10 to facilitate loading of a subject into the generally tubular container 24 for imaging by the imaging system 20. For example, the illustrated subject table 34 includes a movable table or pallet 36 (shown in partially extended position by dotted lines in FIG. 1) for moving a subject into the interior 26 of the tubular container 24 for imaging, and for retracting the subject from the interior 26 back to the isolation region 10 after imaging. The subject table 34 optionally includes an evacuation button or other mechanism for effectuating rapid removal of the specimen from the tubular container 24.

In addition to the illustrated subject table 34, selected other components of the imaging system 20 may be disposed in the isolation region 10, such as one or more local radio frequency coils (an example surface coil 38 being shown in FIG. 1) in the case of an MR scanner portion of the imaging system 20. Alternatively or additionally, one or more whole-body or other types of radio frequency coils may be disposed outside the isolation region 10, for example concentrically within the bore space 22, in the case of an MR scanner portion of the imaging system 20. In some contemplated embodiments, remote controls (either wireless or wired using wires passing through the containment barriers of the isolation region 10 via suitable sealed passthroughs) enable personnel within the isolation region 10 to partially or completely operate the imaging or radiation therapy system 20 by remote control from within the isolation region 10. Additionally or alternatively, the imaging or radiation therapy system 20 may be operated directly from within the less isolated or non-isolated region 12.

The tubular or otherwise-shaped container 24 is suitably made of TBD, fiberglass coated with an epoxy gelcoat, or another material selected for its mechanical properties, impermeability to air and contaminants, and optical transparency, radiation transparency, non-magnetic nature, or other characteristics enabling operative communication between the imaging or radiation therapy system 20 and the subject in the interior 26 of the container 24. The container may be primarily made of a material providing operative communication between the imaging or radiation therapy system and the subject, or may be primarily made of a material that does not provide such operative communication and further include one or more sections, such as viewing windows, that provide the operative communication with the imaging or radiation therapy system.

The containment tube optionally further includes one or more access points 39 (shown only in the perspective view of FIG. 2 as an illustrative example) to allow for general access to the specimen within the containment tube without breaking containment. Such access points optionally include a generally flexible and stretchable material 39f, that allows for containment and can tolerate repetitive decontamination. Optionally, the access points 39 are flush with the tube to allow for easy decontamination. The access points 39 optionally include a rigid seal overlay 39s (shown as a hinged element in an open position in example FIG. 2) that protects the flexible portion 39f from inadvertent pressure. The rigid seal 39s optionally also assists in containment. In some contemplated embodiments, such access points 39 include one or more glove box units (not shown) built into the walls of the tubular container 24 to allow indirect handling of the subject while said subject is disposed within the interior volume 26 of the tubular container 24. Such an arrangement advantageously provides convenient manipulation of the subject, but can complicate decontamination procedures.

With reference to FIGS. 2-4, the illustrated tubular container 24 has a "D" shaped cross-section including a flat portion 40 and an elliptical portion 41. The tubular container 24 is mechanically supported continuously or at distributed discrete points (such as by several spaced apart brackets) along the bore 22, and the flat portion 40 serves as a magnet beam, that is, a surface across which the subject (optionally on the movable table or pallet 36) can be moved into and out of the magnet of the MR scanner portion. In other contemplated embodiments, the tubular container may have a circular or elliptical cross-section, and the subject moved into and out of the tubular container using a table or pallet having dovetailed sides configured to conform with the inner surface of the circular or elliptical tube so as to support the table or pallet at the edges. I-lowever, the flat bottom 40 of the tubular container 24 provides distributed support that is advantageous for loading and unloading of heavy or bulky subjects. Optionally the end cap can be of a clear material such as polycarbonate that will provide visibility of the subject from the non-isolated region 20.

The tubular container 24 includes an endcap member 42 disposed at the end opposite the access opening 30. The endcap member 42 is either integrally formed with the tubular container 24, for example as an integral injection mold or hydroformed component, or is a separate piece that is secured to the tubular container 24 by welding, bonding, mechanical fastening, or so forth. In the latter case the endcap member 42 is suitably either the same material or a different material from the rest of the tubular container 24. The endcap member 42 provides an airtight seal of the end of the tubular container 24 opposite the access opening 30 to ensure fluid isolation of the interior volume 26 from the less isolated or non-isolated region 12.

Figure 6:
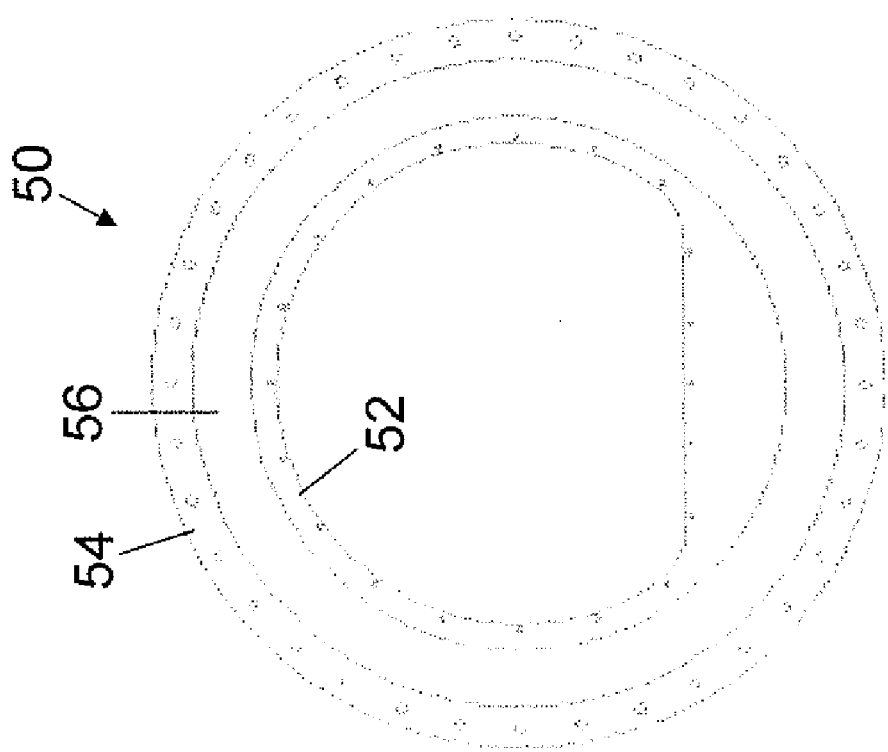
FIGS. 5 and 6 show perspective and front views, respectively, of a gasket for sealing the access opening of the tubular container of FIGS. 2-4 to the containment barrier of the isolation region of FIG. 1.
Figure 5:
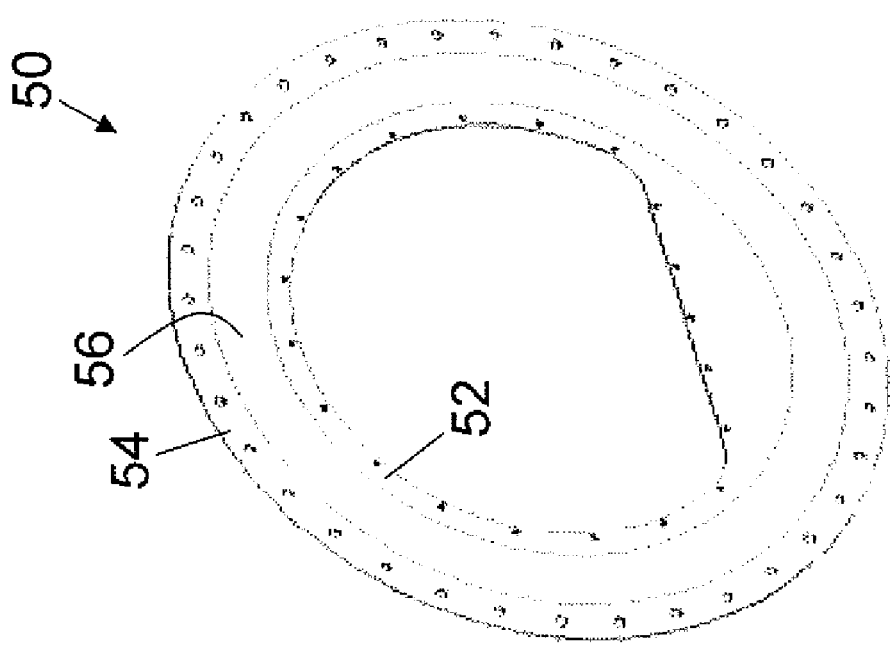

With continuing reference to FIGS. 2-4 and with further reference to FIGS. 5-7 the illustrated tubular container 24 includes an annular flange 44 surrounding the access opening 30. The annular flange 44 is either integrally formed with the tubular container 24, for example as an integral injection mold or hydroformed component, or is a separate piece that is secured to the tubular container 24 by welding, bonding, or so forth. In the latter case the annular flange 44 is suitably either the same material or a different material from the rest of the tubular container 24. The annular flange 44 cooperates with an annular gasket 50 to seal the interface between the containment barrier wall 14 of the isolation region 10 and the tubular container 24. In some suitable embodiments, the containment gasket 50 is a silicone rubber, molded piece that has an elliptical or "D" shaped connection opening 52 for connection to the elliptical or "D" shaped containment tube 24, and a circular outer diameter 54 for connection to the containment wall 14. The gasket 50 also includes a semicircular bubble region 56 that is used to suppress or eliminate vibration transmitted from the containment wall 14 to the containment tube 24 and to accommodate any misalignment of the containment tube 24 with respect to the containment wall 14. The gasket 50 is easily cleanable, with no sharp corners. The containment gasket 50 is mounted to the annular flange 44 of the tubular container 24 and to the containment wall 14 using compression rings. The illustrated gasket 50 is an example; in other embodiments, other types of gaskets may be used, such as an O-ring seal.

The tubular container 24 can be manufactured in various ways, such as by extrusion, injection molding, hydroforming, or so forth. In one approach, the tubular container 24 is manufactured of wound fiberglass coated with epoxy. For a tubular container of circular cross-section, a suitable mandrel for winding the fiberglass filament is suitably made by forming a rough cylindrical shape out of flat plate, and then turning the part on a lathe. However, for non-circular cross-sections such as elliptical or "D" shaped cross-sections, a lathe is not suitable for shaping the mandrel.

Figure 8:
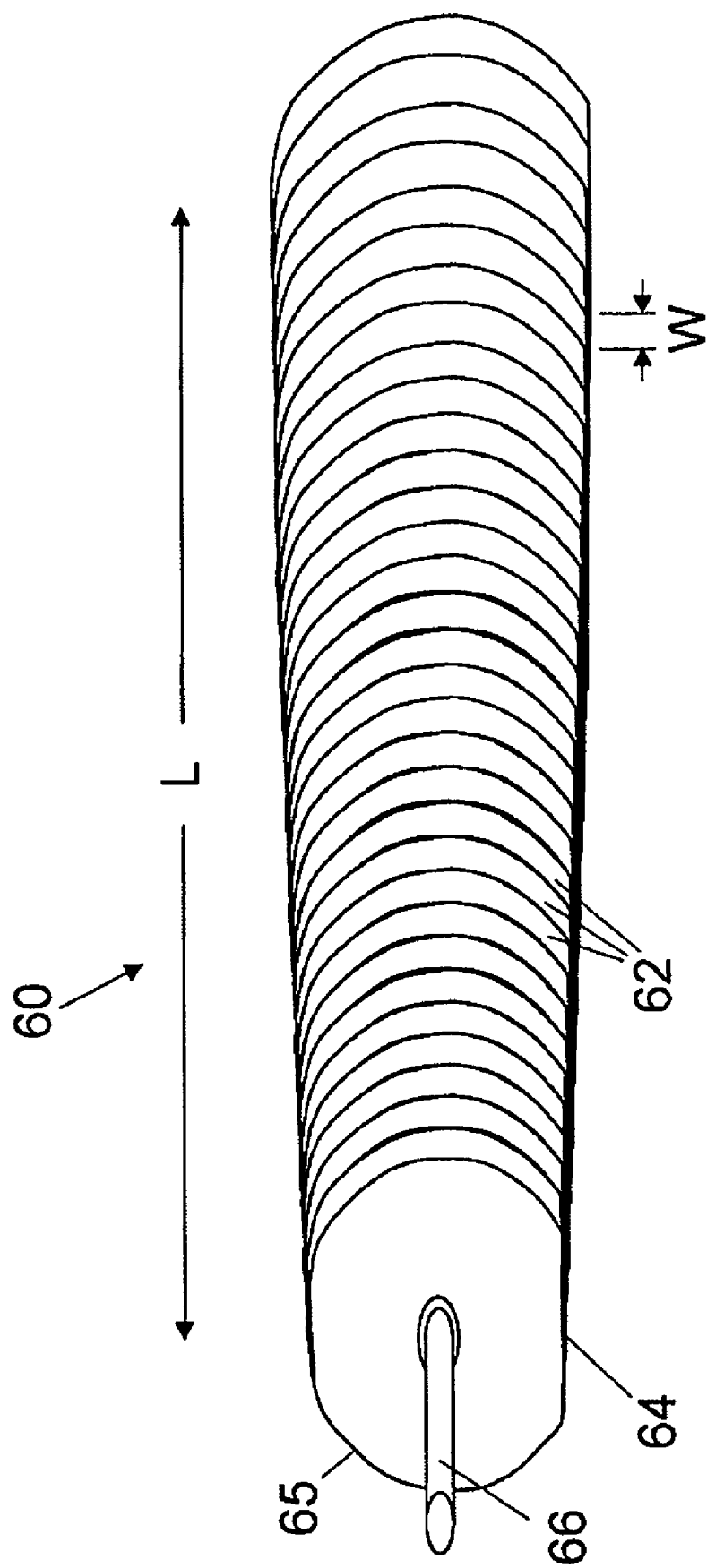
FIG. 8 shows a perspective view of a mandrel for fabricating the tubular container of FIGS. 2-4.

Accordingly, with reference to FIG. 8, a mandrel 60 for winding fiberglass filament to form a tubular container 24 having a "D" shaped or other non-circular cross-section is suitably formed as follows. A plurality of flat, relatively thin plates 62 are generated using vertical milling or another suitable technique. The plates are cut to the desired cross-section, such as the illustrated "D" shaped cross-section having a flat bottom portion 64 and an elliptical portion 65. Each plate 62 has a width W that is substantially thinner than the desired longitudinal length L of the mandrel 60 (and hence of the to-be-generated wound tubular container 24). The plates 62 are pinned, bolted, or otherwise secured together to achieve the needed length L of mandrel 60. A shaft 66 is passed through holes or openings in the plates 62 placed along the centerline of the plates 62 to provide an axis for rotating the mandrel 60 during winding of the fiberglass filament. The plates 62 are optionally of different cross-sectional sizes, and are secured together in an order that imparts to the tubular mandrel 60 a gradual longitudinal cross-section tapering from one end of the tubular mandrel to the other end of the tubular mandrel along the length L. This optional tapering facilitates removal of the wound fiberglass filament structure after curing. The mandrel 60 is suitably polished or sanded to remove any burs or edges after assembly. The fiberglass filament is then wound to define the general shape of the tubular container 24, the epoxy cured, and the structure removed from the mandrel 60. Optionally, a Gelcoat or other surface coating or treatment is applied to the interior of the wound fiberglass tubular container to provide a smooth, cleanable surface.

With returning reference to FIG. 1, the tubular container 24 is suitably held in a substantially stationary position within the bore 22 of the imaging or radiation therapy system 20. In some embodiments, the bracing of the tube at the access end by the annular flange 44 provides sufficient support. However, typically the tubular container 24 is too heavy for single-end bracing, or would undergo unacceptable flexing if supported only at the access end. Moreover, in embodiments such as those of FIGS. 2-4 in which the tubular container 24 includes the flat or otherwise shaped portion 40 configured to serve as a magnet beam or other subject support, the bracing of the tube should be sufficient to support not only the weight of the tube itself but also the weight of the subject and any associated support equipment such as the movable table or pallet 36. In some embodiments, the annular flange 44 provides some support, and an additional brace 70 disposed in the less isolated or non-isolated region 12 provides support for the tubular container 24 at the end opposite the access end. Optionally, a support 72 is disposed in the bore 22 of the imaging or radiation therapy system 20 between the tubular container 24 and the inner surface of the bore 22, and supports at least some weight of the tubular container 24 (and optionally its contents) against the bore 22. The optional support 72 can be in addition to the end-brace 70, or in place of the end-brace 70. Advantageously, the brace 72 is under the pallet 36 when the pallet is fully extended, so that the weight of the subject and pallet 72 are transferred through the proximate portion of the tubular container 24 directly to the underlying brace 72 without being distributed over a large unsupported area of the containment tube 24.

Figure 9:
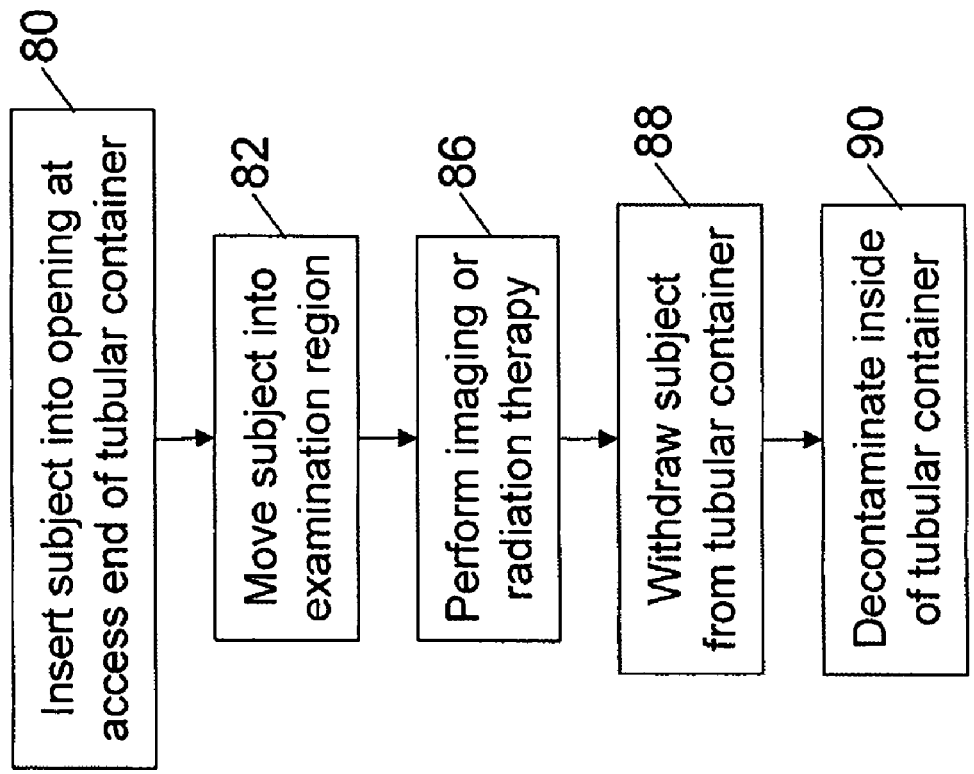
FIG. 9 shows a block diagram of a imaging or radiation therapy process suitably performed by the system of FIG. 1.

With continuing reference to FIG. 1 and with further reference to FIG. 9, a suitable imaging method is described. In a first operation 80, a subject is inserted into the opening 30 of the tubular container 24. If the subject is a live test animal, it may be anesthetized, isolated in a separate soft or hard container, or physically restrained before the insertion 80. In some embodiments, the subject is placed onto the tabletop or pallet 36 that is then extended into the opening 30. The insertion 80 may also include other preparatory operations, such as mounting the magnetic resonance surface radio frequency coil 38 near or on the subject. The subject is then moved through the tube 24 in an operation 82 to the examination region of the imaging or radiation therapy system 20. This can be accomplished, for example, by extending the tabletop or pallet 36 into the tube 24, or by using a push-pull rod, or so forth. In some embodiments, a fail-safe sensor 84, such as a limiter switch, is provided at the end of the tubular container 24 to detect if the subject is moved too far into the tube so as to avoid having the subject from impinging upon the endcap 42 and possibly breach containment. Once the subject is positioned in the examination region, the imaging or radiation therapy system 20 is used to perform selected imaging or therapy operations 86. After imaging or radiation therapy is completed, the subject is withdrawn from the tubular container 24 in an operation 88, for example by retracting the tabletop or pallet 36, by using a pulling hook on a push-pull rod, or so forth. In some embodiments, a quick-extraction mechanism is provided to enable the subject to be withdrawn from the tubular container 24 quickly in the event of a containment breach or other mishap. For example, the subject table 34 optionally includes an emergency retraction mechanism for rapidly withdrawing the tabletop or pallet 36 from the tube 24. Optionally, the interior of the tubular container 24 is decontaminated in an operation 90 after the subject is removed. In other embodiments, decontamination is performed less frequently, for example once-a-week.

Figure 10:
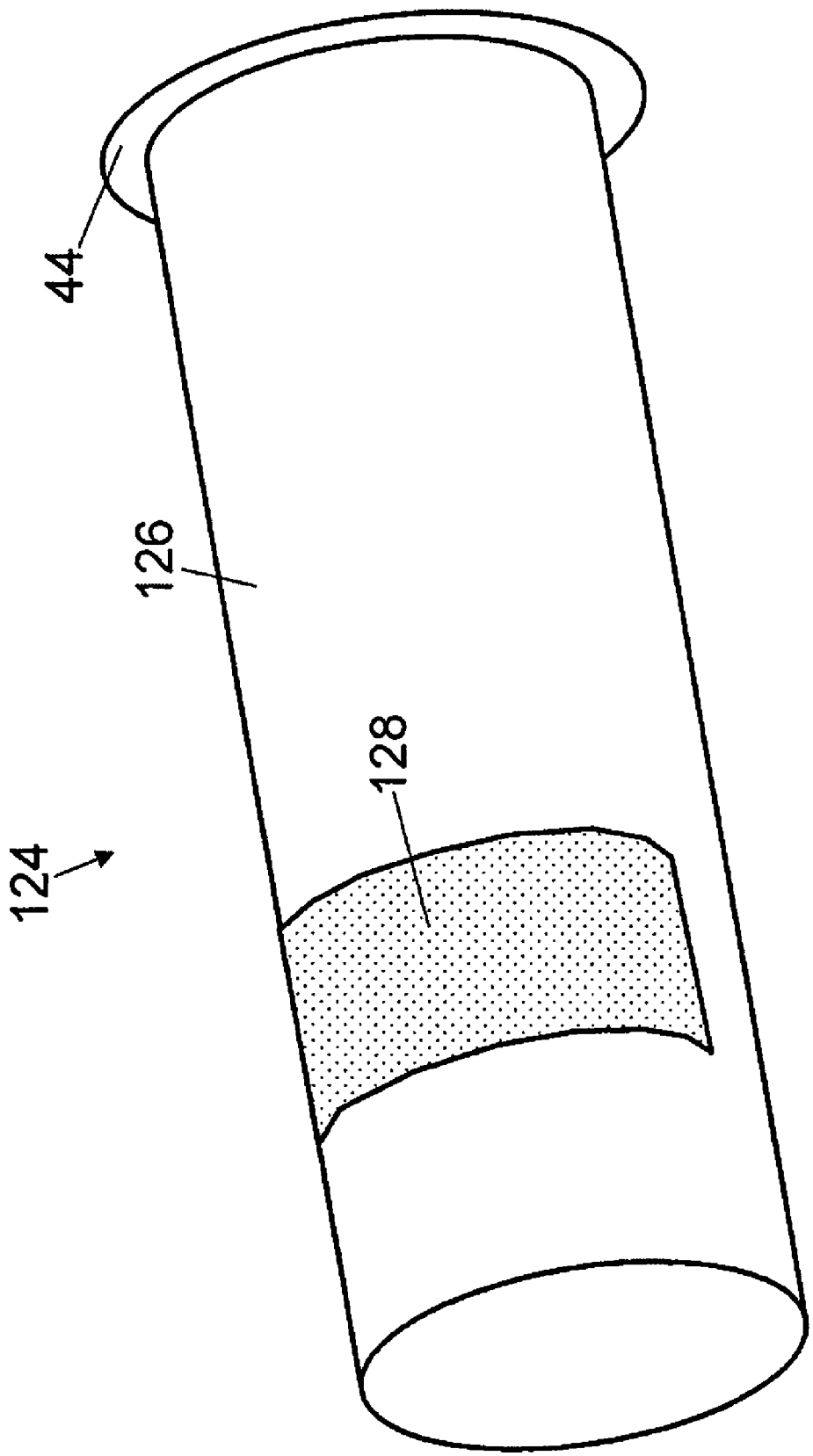
FIGS. 10-12 show some alternative tubular containers suitably substituted for the tubular container of FIGS. 2-4 in the system of FIG. 1.

With reference to FIG. 10, another embodiment of a tubular container 124 is described, that is suitably substituted for the tubular container 24 in the system of FIG. 1. The tubular container 124 includes a sturdy tubular main portion 126, which is typically translucent or opaque respective to the imaging or radiation therapy system 20, and a transparent window portion 128 through which the imaging or radiation therapy system 20 interacts with the subject. The transparent window portion 128 is suitably sealed at its edges to the main portion 126 by a weld, epoxy bond, or other airtight seal. A lower portion of the tubular container 124 is optionally reinforced, for example, by thickening of the bottom of the sturdy main portion 126, to provide enhanced structural rigidity and strength.

Figure 11:
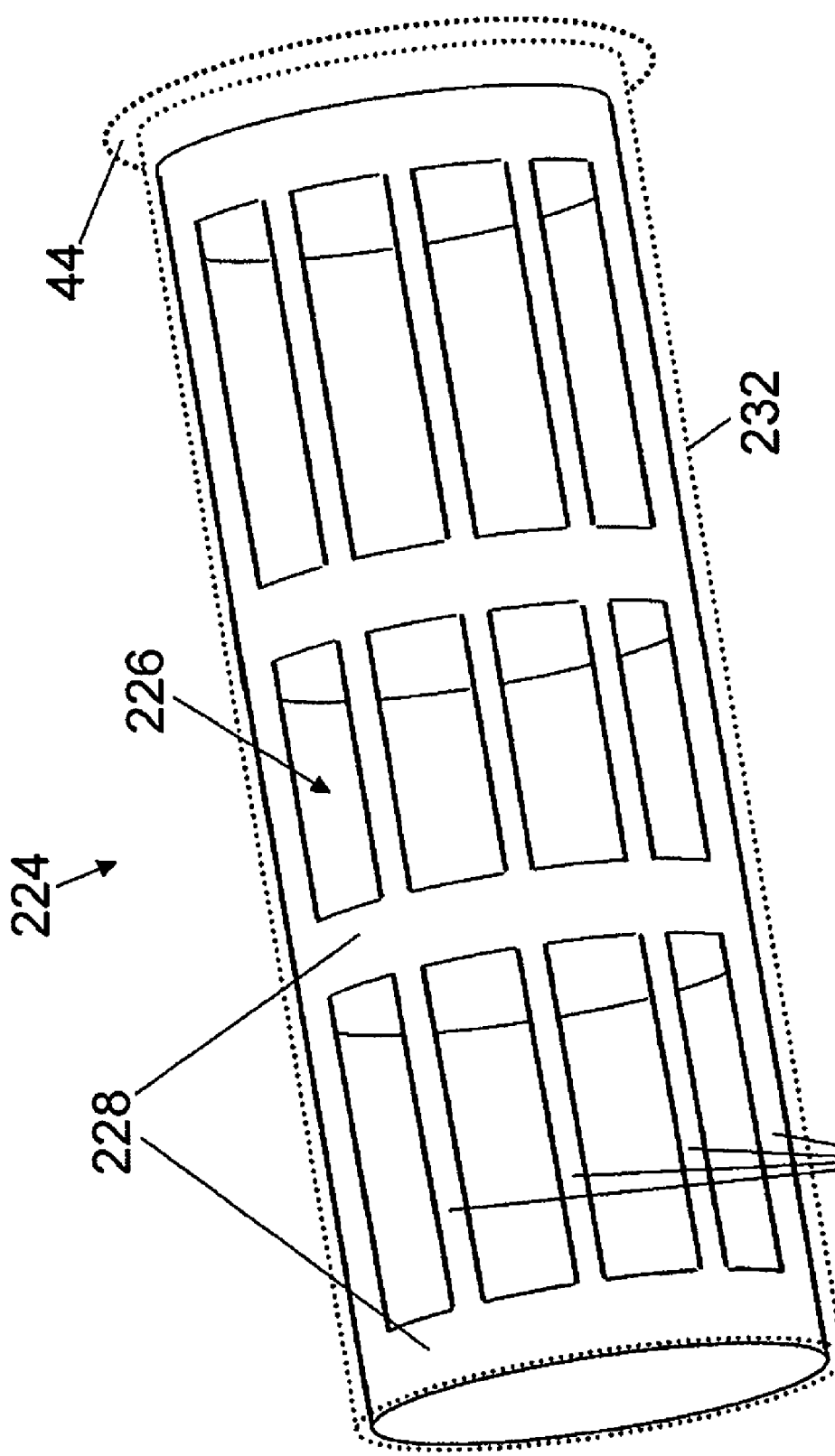

With reference to FIG. 11, another embodiment of a tubular container 224 is described, that is suitably substituted for the tubular container 24 in the system of FIG. 1. The tubular container 224 includes a rigid frame 226 made of annular portions 228 and connecting rods 230. The rigid frame 226 has substantial gaps between the annular portions 228 and the rods 230, and hence is not sealed. A sealing sheath 232 conformably surrounds and is supported by the rigid frame 226.

For an imaging system such as PET, SPECT, CT, or so forth that uses directional radiation, or for a radiation therapy system, the rigid frame 226 can be transparent, translucent, or opaque respective to the radiation while the sealing sheath 232 is transparent. Accordingly, the imaging or therapy system 20 interacts with the subject in the examination region through the sealing sheath 232 at the gaps in the rigid frame 226, and optionally also through the rigid frame 226 if the frame is transparent or translucent. In the latter case, it is contemplated to weight acquired imaging data based on whether it was acquired through the sealing sheath 232 only (that is, through the gaps in the rigid frame 226) or through the sheath 232 and rigid frame 226. If the additional attenuation by the frame 226 is expected to degrade the imaging data, then such weighting advantageously emphasizes the imaging data collected through the gaps which is more reliable.

On the other hand, if the rigid frame 226 is opaque to the directed radiation of the imaging or radiation therapy system 20, then the angular span of acquired imaging data may have gaps corresponding to the connecting rods 230 through which data are not acquired. To accommodate an opaque frame in such a configuration, it is contemplated to arrange the tubular container 224 with a rotatable connection at the containment wall 14, so that by rotating the tubular container 224 the angular intervals blocked by the connecting rods 230 can be moved to enable acquiring a full 180° or 360° dataset. The rotatable connection can enable either complete rotation, or partial rotation over a selected angular interval. In another approach for accommodating an opaque frame in the case of certain types of imaging such as SPECT or CT in which projection data acquired at opposing 180° positions are nominally identical, the angular spacing of the connecting rods 230 can be selected so that complementary angular data 180° away from a connecting rod is always available. For example, if five rods are positioned at 0°, 72°, 144°, 216°, and 288°, then complementary projection data at 180°, 252°, 324°, 36°, and 108° are available.

Figure 12:
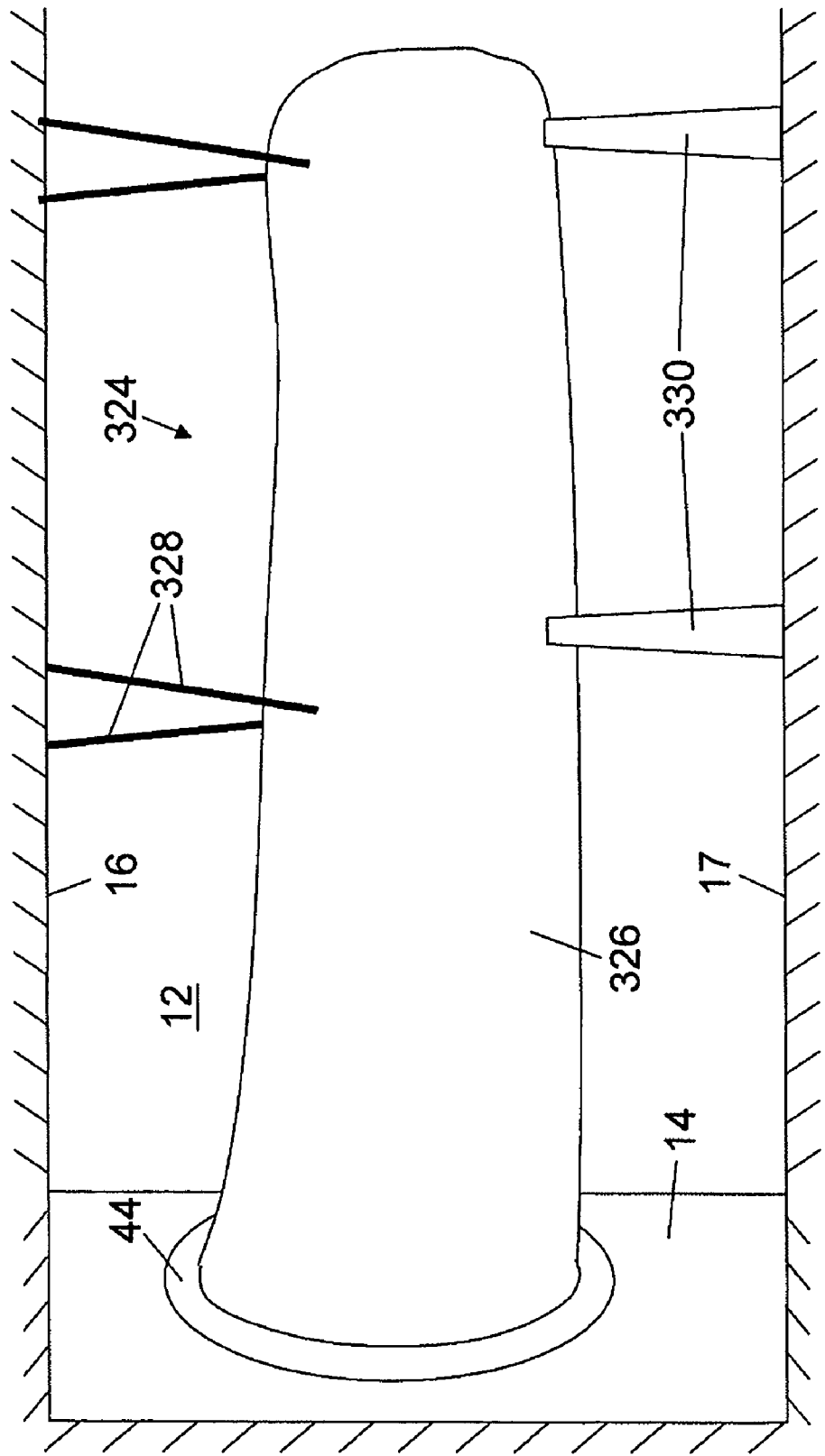

With reference to FIG. 12, another embodiment of a tubular container 324 is described, that is suitably substituted for the tubular container 24 in the system of FIG. 1. The tubular container 324 includes a flexible generally tubular containment bag 326 having an open end sealed to the containment wall 14 separating the isolation region 10 and the less isolated or non-isolated region 12 by the annular flange 44. The flexible containment bag 326 is supported in an expanded configuration by overhead suspenders 328 connected to the ceiling 16 and by lower anchors 330 extending from the floor 17. Optionally, the connections of the suspenders 328 and anchors 330 are detachable so that the flexible containment bag 326 can be rolled up against the wall 14 when not in use, thus freeing up substantial space in the isolated or non-isolated region 12 for other uses. In some embodiments, it is contemplated for the generally tubular containment bag to be made of an elastic material such that the bag "springs back" against the wall 14 when released from the suspenders 328 and anchors 330.

Figure 13:
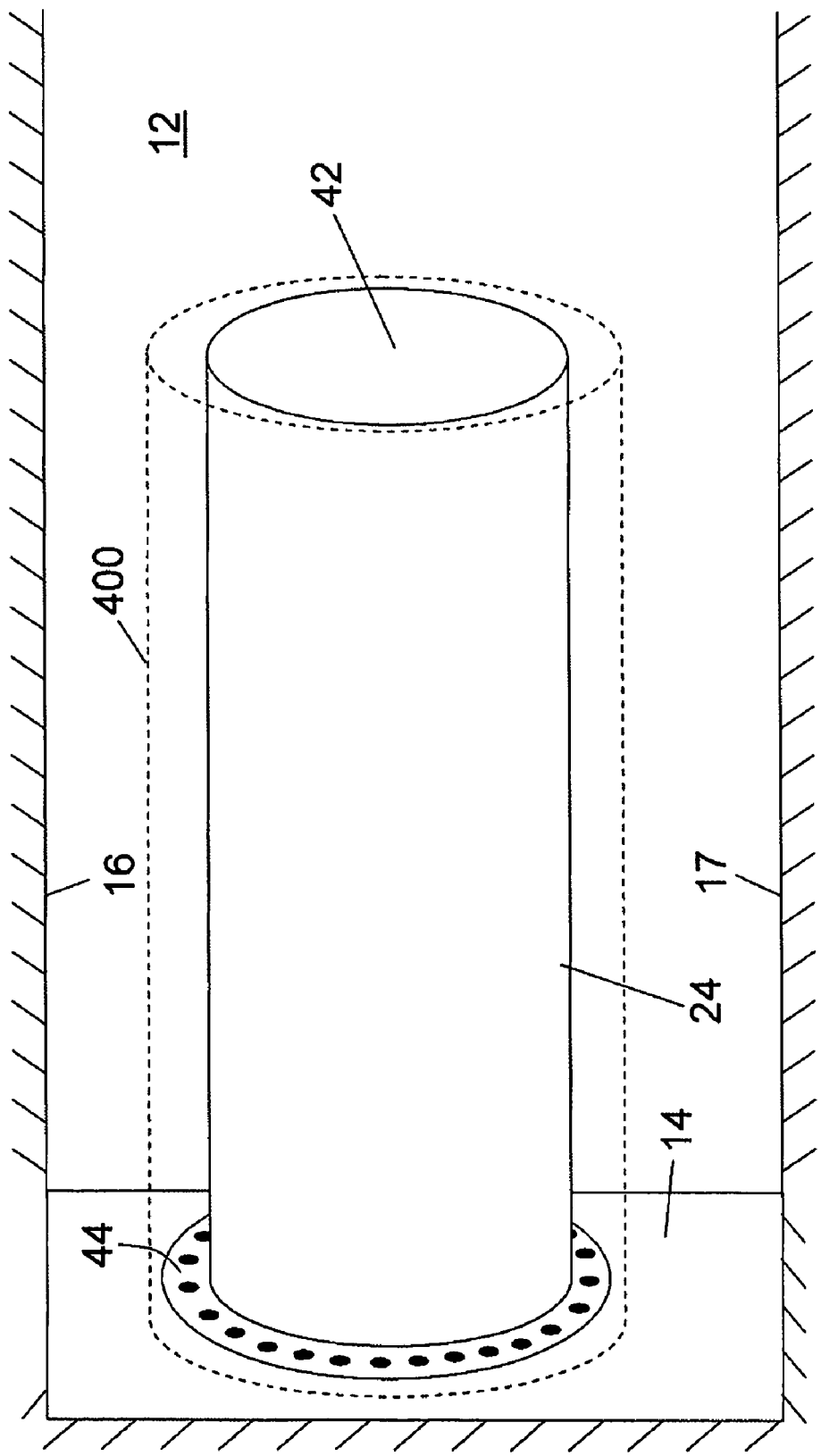
FIG. 13 shows an embodiment of the isolation region FIG. 1 with an additional containment jacket disposed over the tubular container.

With reference to FIG. 13, optionally further measures are taken in the less isolated or non-isolated region 12 to ensure that there is no breach of containment via the tubular container 24. In the illustrated example of FIG. 13, a containment jacket 400 (shown in phantom by dashed lines in FIG. 13 is disposed around the tubular container 24. The containment jacket 400 can be a permanent secondary sealed container to provide double containment, or can be an unsealed container that reduces the likelihood of a breach of the inner tubular container 24 causing contamination of the less isolated or non-isolated region 12. In some embodiments, the containment jacket 400 is not a permanent structure, but rather is a bag or sleeve that can be disposed over the tubular container 24 in an emergency to help seal a breach of the tubular container 24. For example, the containment jacket 400 can be a flexible bag with a sealable end secured to the containment wall 14 on the side of the less isolated or non-isolated region 12, so that it can be extended away from the wall 14 and over the tubular container 24 in the event of an emergency. In another contemplated embodiment, the containment jacket 400 is optionally a clamshell jacket or other automated outer enclosure that activates in the event that an air sensor or other sensor detects a breach of the tubular container 24. In some embodiments, an air flow or partial vacuum is maintained inside the containment jacket 400 to provide flushing or negative differential pressure to help keep contaminants out of the less isolated or non-isolated region 12 in the event of a breach of the container 24. Other contemplated options for limiting the adverse effects of a breach of containment include providing an airtight shutter at the opening 30. The additional containment jacket 400 is optional, and is suitably omitted if the tubular container 24 is expected to provide sufficient containment, or if the isolation region 10 is a moderate risk region, such as a biological laboratory maintained at a level less than BSL-4.

In some environments, the tubular container 24 with its opening 30 providing fluid communication with the isolation region 10 may be undesirable. To provide still further containment, it is contemplated to omit the opening 30 and instead configure the container as a wholly sealed unit that is physically transported from the isolation region 10 to the less isolated region 12 through a suitable airlock or other containment mechanism.

Figure 14:
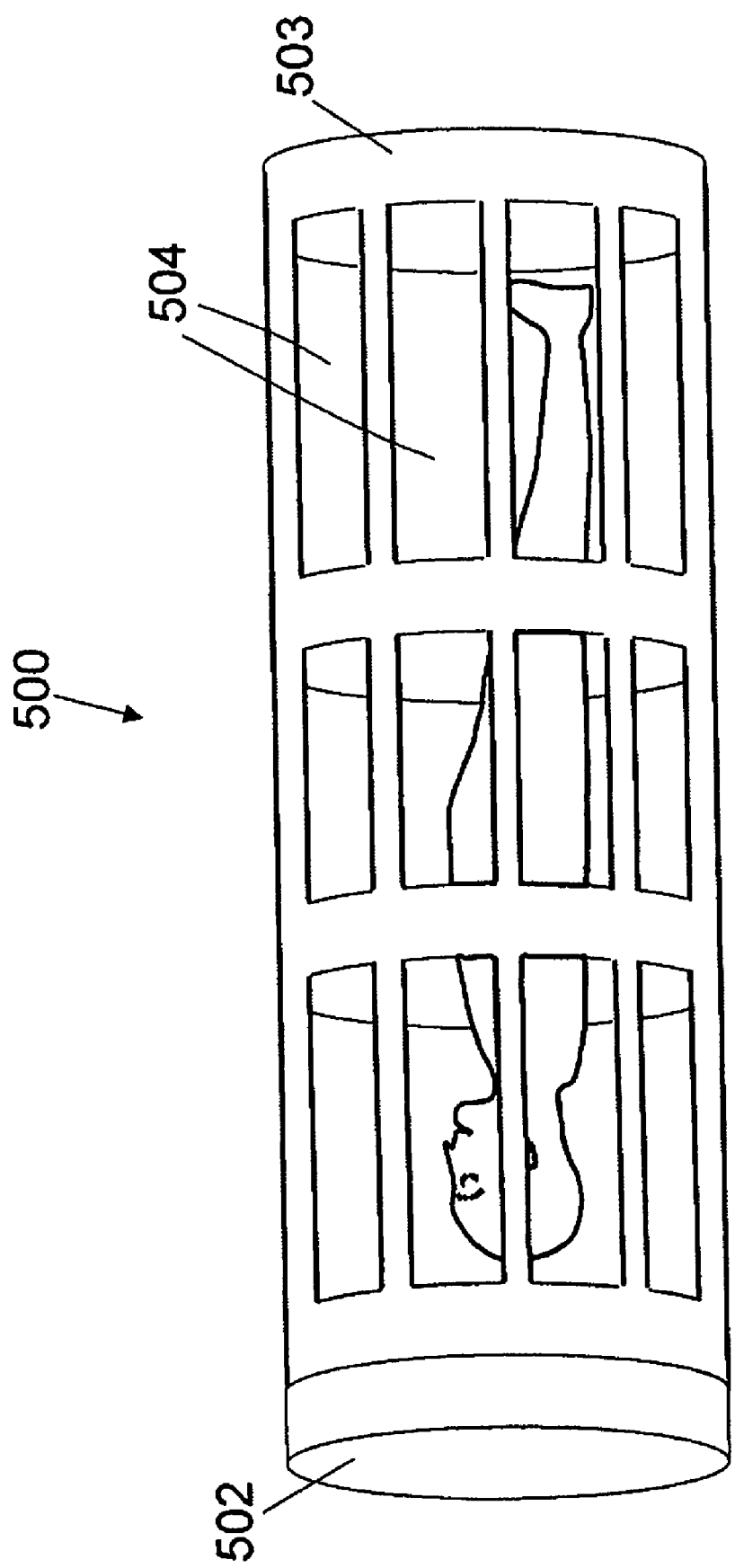
FIG. 14 shows a perspective view of a fully sealed container for transporting a subject from the isolation region to the imaging or radiation therapy system.

With reference to FIG. 14, a tubular container 500 is sized to receive a human subject, and is self-contained when a loading opening at one end is sealed by a removable end cap 502. The opposite end includes a permanent end cap 503; alternatively, two removable end caps can be provided. The removable end cap 502 is sealed to the remainder of the container 500 by an airtight seal formed by welding, bonding, or so forth. Because welding or bonding can be uncomfortable and disturbing to the patient, in some embodiments the end cap 502 is sealed using a gasket, such as a gasket similar to the gasket 50 used to connect the containment tube 24 to the containment wall 14 in the embodiments of FIGS. 1-7. In some example embodiments, the removable end cap 502 may be a one-time use end cap that is welded or otherwise sealed to the container 500 in such a way that when it is subsequently removed it cannot be reused. In some other example embodiments, the end cap is reusable, and is sealed to the container 500 using a copper gasket (not shown) and sealing bolts similar to the type of metal gasket seal used in connecting to a flange of a high vacuum system. The tubular container 500 also preferably includes sealed windows 504 to enable the human subject to see out so as to reduce a likelihood of claustrophobia, and to enable personnel to visually monitor the human subject from outside the sealed container 500.

With reference to FIG. 14, the container 500 is initially disposed on a table 506 or other secure positioning in the isolation region 10, and is loaded with the human subject while disposed in the isolation region 10. The end cap 502 (shown detached in FIG. 14) is sealed to the container 500 after the human subject is loaded. Although not illustrated, when the container 500 is sealed by the end cap 502 the human subject is provided with a supply of breathable air, either through a sealed air feed through passing into the container 500 or by providing an self-contained breathing apparatus within the container 500. (If the human subject is a cadaver, as may be the case for example in a post-mortem analysis of a victim of an unknown disease, then the breathable air supply is suitably omitted).

Figure 15:
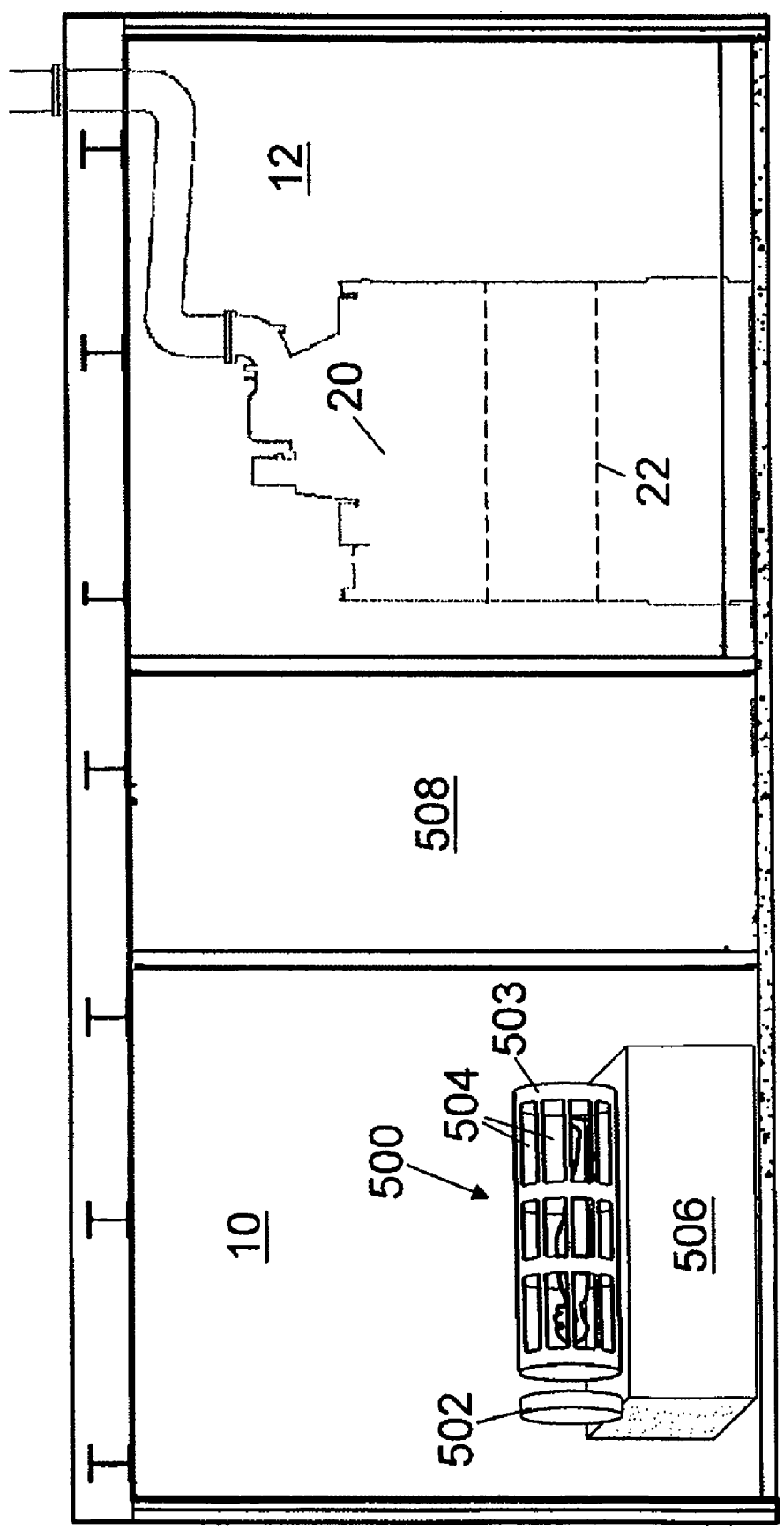
FIG. 15 shows the container of FIG. 14 disposed in the isolation region during loading of the human subject, before sealing using the removable end cap.
Figure 16:
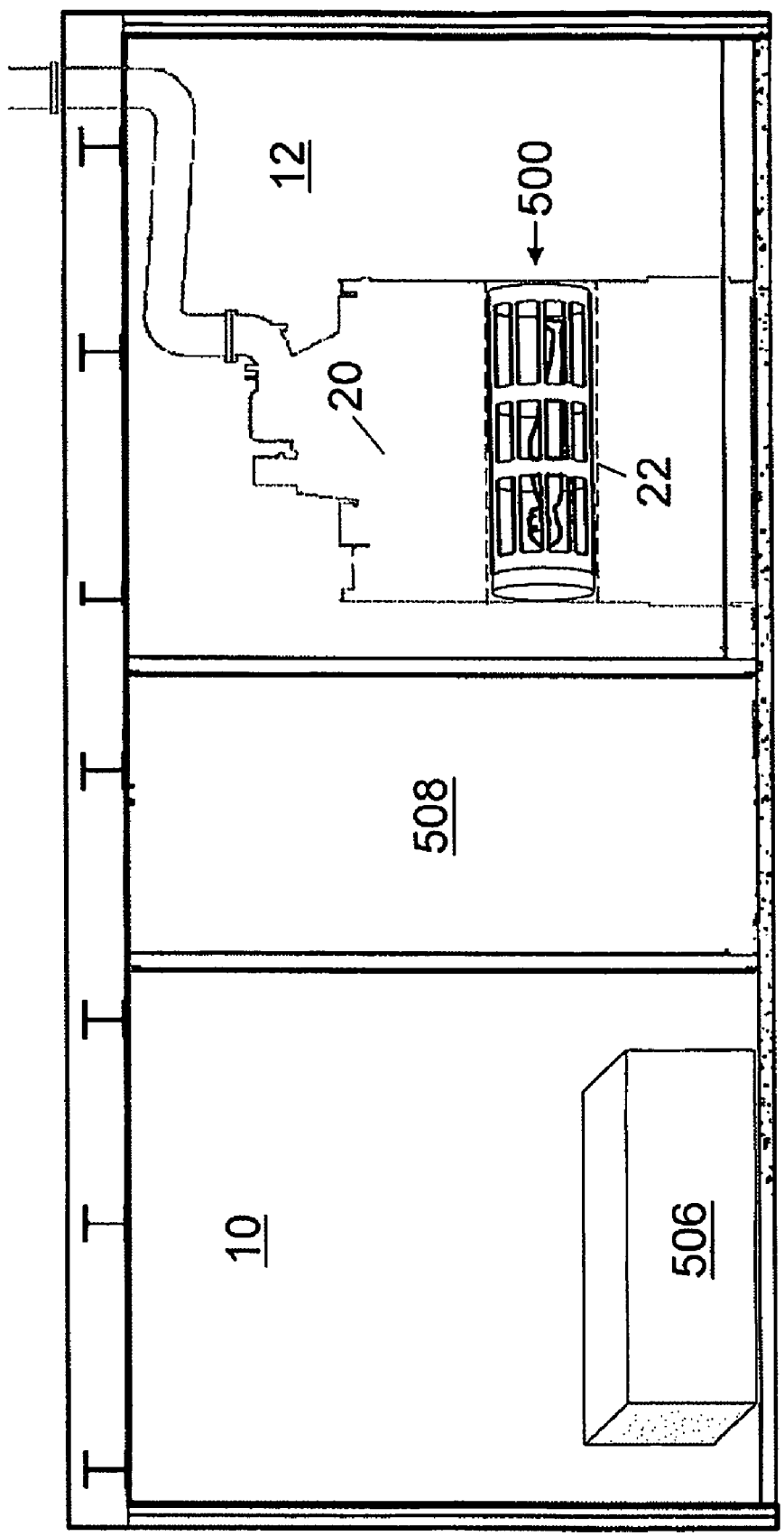
FIG. 16 shows the fully sealed container of FIG. 14 in the less isolated or non-isolated region and in position for imaging or radiation therapy.

With reference to FIG. 15, once the container 500 is sealed with the human subject inside, it is transferred from the isolation region 10 to the less isolated or non-isolated region 12 via one or more airlocks 508 (diagrammatically shown in FIGS. 15 and 16) or other suitable isolation mechanisms disposed between the isolation region 10 and the less isolated or non-isolated region 12. The outside of the sealed container 500 is decontaminated before entry into the less isolated or non-isolated region 12. In one suitable approach, initial decontamination is performed after sealing of the end cap 502 while the sealed container 500 is still in the isolation region 10, followed by more thorough or repeated decontamination of the sealed container 500 performed in the airlock room or compartment 508 passing out of the isolation region 10. Once the sealed and externally decontaminated container 500 is moved into the less isolated or non-isolated region 12, the container 500 is suitably sized and shaped for insertion into the bore 22 of the imaging or radiation therapy system 20. For example, the illustrated cylindrical container 500 conformably slides into the cylindrical bore 22 of the imaging or radiation therapy system 20 so that it is stably and rigidly fixed positioned inside the bore 22. Alternatively, the container can include anchor points for braces, clamps, or other securing devices for securing the container in the bore or other examination region of the imaging or radiation therapy system. Imaging or radiation therapy is performed on the human subject while in the bore 22. Afterward, the container 500 is transferred back to the isolation region 10 via the airlock room or compartment 508 (without decontamination in this case), and the sealed end cap 502 is unsealed and removed to allow removal of the human subject.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. An imaging or treatment method comprising:
    surrounding a human subject with a sealed container while the human subject is disposed in an isolation region;
    transporting the sealed container from the isolation region to an imaging or treatment apparatus with the human subject disposed in and surrounded by the sealed container; and
    performing imaging or treatment of the human subject surrounded by the sealed container using the imaging or treatment apparatus;
    wherein the sealed container is sized and shaped for insertion into a cylindrical bore of the imaging or treatment apparatus and the transporting includes conformably sliding the sealed container into the cylindrical bore of the imaging or treatment apparatus.

2. The imaging or treatment method as set forth in claim 1, wherein the transporting further comprises:
    after the surrounding, decontaminating an exterior of the sealed container.

3. The imaging or treatment method as set forth in claim 1, further comprising:
    disposing the human subject in the container;
    sealing the container using a sealing portion configured to seal the container with a human subject inside; and
    after the sealing, decontaminating the container.

4. The imaging or treatment method as set forth in claim 1, wherein the transporting includes transferring the sealed container with the human subject disposed in and surrounded by the sealed container out of the isolation region via one or more airlocks.

5. An imaging or treatment method comprising:
    surrounding a human subject with a sealed container while the subject is disposed in an isolation region;
    transporting the human subject surrounded by the sealed container from the isolation region to an imaging or treatment apparatus;
    performing imaging or treatment of the human subject surrounded by the sealed container using the imaging or treatment apparatus; and
    providing breathable air to the human subject surrounded by the sealed container by providing a self-contained breathing apparatus within the sealed container.

6. An imaging or treatment method comprising:
    extending a flexible sheath or containment bag away from a wall separating an isolation region from an imaging or therapy system into an extended configuration, the flexible sheath or containment bag in the extended configuration defining an interior that overlaps an examination region of the imaging or therapy system and is isolated from the imaging or therapy system by the flexible sheath or containment bag, the interior being in fluid communication with the isolation region via an opening in the wall sized to admit a subject from the isolation region into the interior overlapping the examination region, wherein the flexible sheath or containment bag is elastic and the extending comprises biasing the elastic flexible sheath or containment bag against the elasticity into the extended configuration and retaining the elastic flexible sheath or containment bag in the extended configuration using suspenders or anchors disposed outside of the isolation region; and performing imaging or therapy respective to the subject while the subject is disposed in the interior overlapping the examination region.

7. The imaging or treatment method as set forth in claim 6, further comprising:

after the imaging or therapy, rolling or releasing the flexible sheath or containment bag such that the elastic flexible sheath or containment bag assumes a more compact configuration proximate to the wall.

8. The imaging or treatment method as set forth in claim 6, wherein the flexible sheath or containment bag is tubular in the extended configuration.

9. The imaging or treatment method as set forth in claim 8, wherein the imaging or therapy system defines a tubular bore surrounding the examination region and the tubular flexible sheath or containment bag is disposed coaxially inside the tubular bore in the extended configuration.

10. An imaging or treatment method comprising:

extending a flexible sheath or containment bag away from a wall separating an isolation region from an imaging or therapy system into an extended configuration, the flexible sheath or containment bag in the extended configuration defining an interior that overlaps an examination region of the imaging or therapy system and is isolated from the imaging or therapy system by the flexible sheath or containment bag, the interior being in fluid communication with the isolation region via an opening in the wall sized to admit a subject from the isolation region into the interior overlapping the examination region;

performing imaging or therapy respective to the subject while the subject is disposed in the interior overlapping the examination region; and maintaining an air flow inside the flexible sheath or containment bag at least during the imaging or therapy.

* * * * *